United States Patent
Jonson (10) Patent No.: US 6,578,575 B1
(45) Date of Patent: Jun. 17, 2003

(54) METHOD AND APPARATUS FOR OPTIMIZATION OF MECHANICAL VENTILATION

(75) Inventor: Björn Jonson, Lund (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/647,412

(22) PCT Filed: Apr. 6, 1999

(86) PCT No.: PCT/SE99/00564

§ 371 (c)(1),
(2), (4) Date: Sep. 29, 2000

(87) PCT Pub. No.: WO99/51292

PCT Pub. Date: Oct. 14, 1999

(30) Foreign Application Priority Data

Apr. 3, 1998 (SE) ............................................. 9801175

(51) Int. Cl.⁷ ........................................... A61M 16/00
(52) U.S. Cl. ............................. 128/204.21; 128/204.18
(58) Field of Search ...................... 128/204.18, 204.21, 128/204.26, 204.22, 204.23, 205.23; 600/300, 301, 529, 533, 538, 540

(56) References Cited

U.S. PATENT DOCUMENTS

| | | | | |
|---|---|---|---|---|
| 5,535,738 A | * | 7/1996 | Estes et al. ............ | 128/204.21 |
| 5,678,539 A | * | 10/1997 | Schubert et al. ....... | 128/204.21 |
| 5,878,744 A | * | 3/1999 | Pfeiffer ................. | 128/204.22 |
| 5,881,723 A | * | 3/1999 | Wallace et al. ........ | 128/204.18 |
| 5,915,379 A | * | 6/1999 | Wallace et al. ........ | 128/204.18 |
| 5,915,380 A | * | 6/1999 | Wallace et al. ........ | 128/203.12 |
| 5,931,160 A | * | 8/1999 | Gilmore et al. ........ | 128/204.18 |
| 5,937,853 A | * | 8/1999 | Strom ................... | 128/204.18 |
| 6,135,105 A | * | 10/2000 | Lampotang et al. ... | 128/204.18 |
| 6,148,814 A | * | 11/2000 | Clemmer et al. ...... | 128/200.24 |
| 6,158,432 A | * | 12/2000 | Biondi et al. .......... | 128/204.21 |

OTHER PUBLICATIONS

"Respiratory Mechanics During Mechanical Ventilation in Health and in Disease," Svantesson, Department of Clinical Physiology, Lund University, Sweden (1997) * See attached office Action for Explanation.

"A Single Computer–controlled Mechanical Insufflation Allows Determination of the Pressure–volume Relationship of the Respiratory System," Svantesson et al., Journal of Clinical Monitoring and Computing, vol. 15 (1999), pp. 9–16.

Abstract for Swedish Patent 506521.

* cited by examiner

Primary Examiner—Weilun Lo
Assistant Examiner—Teena Mitchell
(74) Attorney, Agent, or Firm—Schiff Hardin & Waite (57) ABSTRACT

In order to select an optimal ventilation mode for mechanically ventilating a patient, from among a number of ventilation modes, a mathematical description of the patient's respiratory system is produced in a computer from measured parameters related to properties of the respiratory system, and in the computer the mathematical descriptions for different modes of ventilation are tested on the mathematical description to obtain simulated results. An operator can selected a mode of ventilation to be analyzed by comparing the simulated results with a therapeutic goal, so that an optimal ventilation mode can be selected. Alternatively, the computer can iteratively test a number of modeled ventilation modes to identify the ventilation mode which comes closest to the therapeutic goal.

13 Claims, 7 Drawing Sheets

LUNG PHYSIOLOGY

Pel/V CURVE

| | |
|---|---|
| Vmin | -69 |
| Plip | 13.2 |
| Vlip | 283 |
| Clin | 46.4 |
| Vuip | 813 |
| Vmax | 1567 |

RESISTANCE

| | |
|---|---|
| r0 (insp.) | 7.21 |
| r1 (insp.) | -0.001 |
| g0 (exp.) | 0.0389 |
| g1 (exp.) | 8E-05 |

$CO_2$ ELIMINATION

| | |
|---|---|
| a$CO2$ | -2.7 |
| b$CO2$ | 0.014 |
| c$CO2$ | 1E-05 |

TUBE RESISTANCE

| | |
|---|---|
| K_1 | 6 |
| K_2 | 7.78 |

MODE OF VENTILATION

| | CURRENT | ALTERNATIVE |
|---|---|---|
| MIN_VOL, lit | 11.0 | 14.0 |
| Frekv, min-1 | 20 | 30 |
| Ti % | 25 | 25 |
| RAMP | 0 | 0 |
| $Pe_{start}$ | 4 | 4.0 |
| $Pe_{end}$ | 4 | 4.0 |

| OUTCOME | CURRENT | ALTERNATIVE |
|---|---|---|
| Vt, ml | 550 | 467 |
| Ptr, peak | 25 | 25 |
| Pel, peak | 20 | 19 |
| Ptr, meanl | 9 | 10 |
| Pel, mean | 11 | 12 |
| PEEP tot | 4.6 | 6.6 |
| $PaCO_2$ mmHg | 40 | 36 |

LUNG PHYSIOLOGY

| Pel/V CURVE | |
|---|---|
| Vmin | -69 |
| Plip | 13.2 |
| Vlip | 283 |
| Clin | 46.4 |
| Vuip | 813 |
| Vmax | 1567 |

| RESISTANCE | |
|---|---|
| r0 (insp.) | 7.21 |
| r1 (insp.) | -0.001 |
| g0 (exp.) | 0.0389 |
| g1 (exp.) | 8E-05 |

| $CO_2$ ELIMINATION | |
|---|---|
| aCO2 | -2.7 |
| bCO2 | 0.014 |
| cCO2 | 1E-05 |

| TUBE RESISTANCE | |
|---|---|
| K_1 | 6 |
| K_2 | 7.78 |

| | CURRENT | GOAL |
|---|---|---|
| $PaCO_2$ mm Hg | 40 | 50 |
| PEEPtot | 4.6 | 10 |

| MODE OF VENTILATION | | | LIMITS | |
|---|---|---|---|---|
| | CURRENT | ALTER-NATIVE | MIN | MAX |
| Vt, ml | 552 | 358 | 200 | 750 |
| Ti % | 25 | 60 | 20 | 60 |
| RAMP | 0 | -86 | -100 | 100 |
| Pe, start | 4 | 0 | 0 | 10 |
| Pe, end | 4 | 0 | 0 | 10 |

| | CURRENT | ALTERNATIVE |
|---|---|---|
| Frekv, min - 1 | 20 | 36 |
| MIN_VOL, lit | 11 | 12.9 |

| OUTCOME | IDEAL | SIMULATED | WEIGHT | ERROR |
|---|---|---|---|---|
| PEEPtot, GOAL | 10 | 9.9 | 2 | 0.02 |
| PEEPtot | MINIMUM | 9.9 | 0 | 0.00 |
| Ptr, peak | MINIMUM | 19 | 1 | 18.86 |
| Pel, peak | MINIMUM | 18 | 0 | 0.00 |
| Ptr, mean | MINIMUM | 13 | 0 | 0.00 |
| Pel, mean | MINIMUM | 15 | 0 | 0.00 |
| | | | SUM | 18.9 |

METHOD AND APPARATUS FOR OPTIMIZATION OF MECHANICAL VENTILATION

BACKGROUND OF THE INVENTION

1. Field of the Invention

The present invention pertains to a method for optimization of ventilator function aiming at that desired therapeutic goals should be reached. The optimization therefor is achieved on the basis of investigated physiological properties of the respiratory system.

2. Description of the Prior Art

Mechanical ventilation may cause lung damage. High pressures lead to damage denoted barotrauma. Ventilation at low pressures and volumes may lead to collapse and re-expansion of lung compartments during expirations and inspirations, respectively. This phenomenon may be denoted Recorex. Recorex may lead to lung trauma because of shear forces between zones of collapsed and aerated lung parenchyma. Studies of lung mechanics and adaptation of mechanical ventilation to lung physiology allow reduction of barotrauma and Recorex. The elastic pressure volume diagram, the $P_{el}/V$ curve, can be recorded, for example with an electronically controlled ventilator.

With one or several $P_{el}/V$ curves recorded under different circumstances one can judge whether the tidal volume, Vt, as a whole or in-part falls within the pressure/volume range within which barotrauma and Recorex are minimal. Under guidance of this information one may change the pattern of ventilation in such a way that an optimal P/V range is used to ventilate the lungs. One may for example increase the positive end expiratory pressure, PEEP, if the lung volume is to low. An alternative is to increase the frequency or to reduce the time for expiration in relation to the time for inspiration so that the lungs during expiration do not empty to a degree such that elastic forces exerted by the thoracic cage and the lungs are equilibrated. Thereby, it is accomplished that the alveolar pressure at the end of expiration is positive, which is denoted auto-PEEP. This implies that the lung volume is increased so that Recorex is avoided. If one rather would find that the pressure should be diminished during inspiration, one may decrease ventilation and thereby lower the peak airway pressure in order to decrease the risk for barotrauma.

Either an increase of PEEP or a lowering of the peak airway pressure frequently lead to a decrease of pulmonary gas exchange which may be deleterious. A lowering of the oxygenation of the blood can be counteracted by an increase in the fraction of oxygen inspired gas. This is, however, associated with risks. Another effect is that $CO_2$-elimination is decreased which implies that carbon dioxide is retained in the body. Lately one has frequently accepted this effect, denoted permissive hypoventilation, however, without improved clinical results. Several physiological mechanisms are dependent on pH and thereby on the partial pressure of $CO_2$ in arterial blood, $PaCO_2$. Accordingly it is important, not only to exercise control over airway pressures but also over gas exchange so that $PaCO_2$ is maintained within suitable limits.

By recording of a so called single breath test for $CO_2$ one may estimate to what extent a change of Vt and minute ventilation, Vmin, will lead to a change of $CO_2$ elimination expressed in ml/min. By measuring, or estimating, how much $CO_2$ elimination changes at a change of breathing pattern one can during the following breaths estimate to what extent the change will lead to a change of $PaCO_2$.

In order to improve the results of mechanical ventilation at grave lung disease both barotrauma and Recorex should be avoided. In order to get around that the gas exchange is unduly affected so that $CO_2$ retention or hypoxia develops one may better use the Vt. by flushing the connecting tubes, particularly the tracheal tube with unspoiled gas during the later part of expiration. Thereby one may decrease the dead space so that one may decrease Vt without the risk for reduced gas exchange.

The pulmonary exchange of carbon dioxide and oxygen are coupled to one another because for each volume of oxygen taken up and consumed through metabolism a thereto proportional volume of carbon dioxide is produced and eliminated. What has been said above about carbon dioxide is accordingly paralleled by a corresponding phenomenon for oxygen. Technically it is more difficult to make fast and accurate determination of oxygen concentration than of carbon dioxide concentration. Particularly, at high inspired oxygen concentrations it is very difficult to accurately measure oxygen uptake. For these reasons carbon dioxide is below focussed upon in discussions about gas exchange although most aspects are relevant also with respect to oxygen.

Strategies for avoidance of lung damage following mechanical ventilation, and even to protect the lungs against damage, is denoted protective lung ventilation, PLV.

U.S. Pat. No. 4,917,080 desribes a method for controlling a ventilating apparatus. In a first simulator the characteristics of the ventilating apparatus is simulated and in a second simulator patient parameters are simulated. An adjustment to the ventilating apparatus can first be processed in the first simulator and the output is coupled to the second simulator to derive an effect of the adjustment as new patient data from the second simulator. The adjustment may then be switched to the ventilating apparatus or entered manually.

SUMMARY OF THE INVENTION

GB 2 093 218 discloses a respirator comprising a screen and controlled by a microprocessor. On the screen curves reflecting the result of new respiratory conditions can be shown. This simulation can be carried out while ventilation takes place with pre-established parameters. If the new values are satisfactory, the operator can request the change in the ventilation of the patient.

One objective of the present invention concerns new principles for determination of how PLV should be performed on the basis of the physiological characteristics of the individual patient and in consideration of the demands of an adequate gas exchange. The invention is founded on measurements of respiratory mechanics and also of gas exchange. The measurements are followed by a mathematical characterisation of these physiological characteristics. Thereafter a computer performs an analysis of the mode of ventilation by the ventilator with the goal that the therapeutic goal defined by the responsible operator (doctor or therapist) is reached. In a typical case the goal is defined as a combination of PLV and adequate gas exchange.

Methods for studies of the mechanics of the respiratory system are previously known, for example through the Swedish patent C2 506521 and Repiratory Mechanics During Mechanical Ventilation in Health and Disease," C. Svantesson, Thesis, Department of Clinical Physiology, Lund University (1997), ISBN 91-682-2766-9 and "A Single Computer-Controlled Mechanical Insufflation Allows Determination of the Pressure-Volume Relationship of the Respiratory System," Svantesson et al., Journal of Clinial Monitoring and Computing (1999). Accordingly, one may use a computer-controlled ventilator to study the mechanics of the respiratory system. A pressure and volume range extending beyond the range of the tidal volume at the current setting of the ventilator, Vt, may be studied. A modification of one expiration by prolongation of the time for expiration and/or by reducing PEEP allows a volume range below the Vt to be studied. A volume range above the Vt may be studied by increasing of the volume of gas that is insufflated during the inspiration following the modified expiration.

The three segments of the sigmoid Pel/V curve are described by an equation in which the elastic recoil pressure is related to the volume, V. The reference volume for V is the lowest observed volume during the measurement. The intermediate segment which begins at the volume Vlip and the pressure Plip is linear and has, accordingly, a constant slope corresponding to a value of compliance denoted Clin. The lower and the upper segments are non-linear. The slopes of these segments (compliance) approach asymptotically zero when the curves are extrapolated towards a low and a high volume, denoted Vmin and Vmax, respectively.

The equation that describes Pel as a function of V can be as follows:

For $V < Vlip$:

$Pel = Plip - (Vlip - Vmin)/Clin * \ln((Vmin - Vlip)/(Vmin - V))$

For $Vlip \leq V \leq Vuip$:

$Pel = Plip + (V - Vlip)/Clin$

For $V > Vuip$:

$Pel = Puip + (Vmax - Vuip)/Clin * \ln((Vmax - Vuip)/(Vmax - V))$ (1)

The pressure that drives flow through the airways can in analogy with Ohm's law be calculated as resistance multiplied by flow rate. Inspiratory resistance, R(i), often varies to a small extent during the breath. It may decrease with increasing lung volume. The pressure that drives flow during inspiration Pres(i), can defined as a function of flow rate, F, and volume, V:

$Pres(i) = (r0 + r1*V)*F$ (2)

r0 denotes the resistance at zero volume, while r1, usually a negative number, gives the variation of R(i) with volume.

Equation 1 and 2 describe the mechanical behaviour of the respiratory system during inspiration under various circumstances. Their coefficients can be determined with known methods. However, simpler equations may often be used. Within a limited volume range a linear equation may with adequate accuracy escribe the $P_{el}/V$ curve. The inspiratory resistance can often be represented by a constant. This invention can be embodied on the basis of other equations, which in the actual situation adequately represent the elastic and resistive properties of the respiratory system. Furthermore, the invention is not dependent upon which method is used for measurement and analysis leading to a mathematical description of the elastic and resistive properties of the respiratory system.

The above object is achieved in accordance with the principles of the present invention in a first embodiment of a method and an apparatus for searching for an optimal mode of ventilation, from among a number of ventilation modes in a ventilator, wherein measuring parameters related to the properties of the respiratory system are obtained, a mathematical description of the respiratory system is formed based on the measured parameters, wherein mathematical descriptions for different modes of ventilation are also formed, wherein the mathematical descriptions are tested for different modes of ventilation using the mathematical description of the respiratory system, in order to determine simulated results, the simulated results are compared with a therapeutic goal, and the mode of ventilation is identified which provides a simulated result that comes closest to the therapeutic goal, the identified ventilation mode being considered the optimal mode.

In a further embodiment of the method and apparatus, instead of comparing the simulated results to the therapeutic goal, an iterative analysis is undertaken by forming a mathematical description of a new, different mode of ventilation, testing the new mathematical description for the new, different mode of ventilation on the mathematical description of the respiratory system to determine a new simulated result for the different mode of ventilation, and the new mathematical description for each new, different mode of ventilation is based on the therapeutic goal, a comparison between the simulated result and the therapeutic goal for previously applied mathematical descriptions, and predetermined limits for changes in parameters between two consecutive new modes of ventilation. Again, the mode of ventilation that provides a simulated result coming closest to a therapeutic goal is selected as the optimal mode.

DESCRIPTION OF THE PREFERRED EMBODIMENTS.

According to a preferred embodiment of the invention the function of the respiratory system i studied with a known system based upon a computer-controlled ventilator complemented with a $CO_2$ analyser, ($CO_2$ analyzer 930, Siemens-Elema, Solna). During a sequence of breaths analogue signals corresponding to flow rate, pressure and $CO_2$ concentration are converted to a digital format and stored. The flow signal is corrected for compression/decompression of the gas in the tubings and is then integrated to a volume signal. The reference level of the latter is the minimum volume during the sequence of breaths. From the pressure measured in the ventilator the pressure in the trachea, Ptr, is calculated by subtraction of the pressure driving flow through connecting tubing. The latter pressure is calculated as the product between flow rate and tube resistance.

Figure 3:
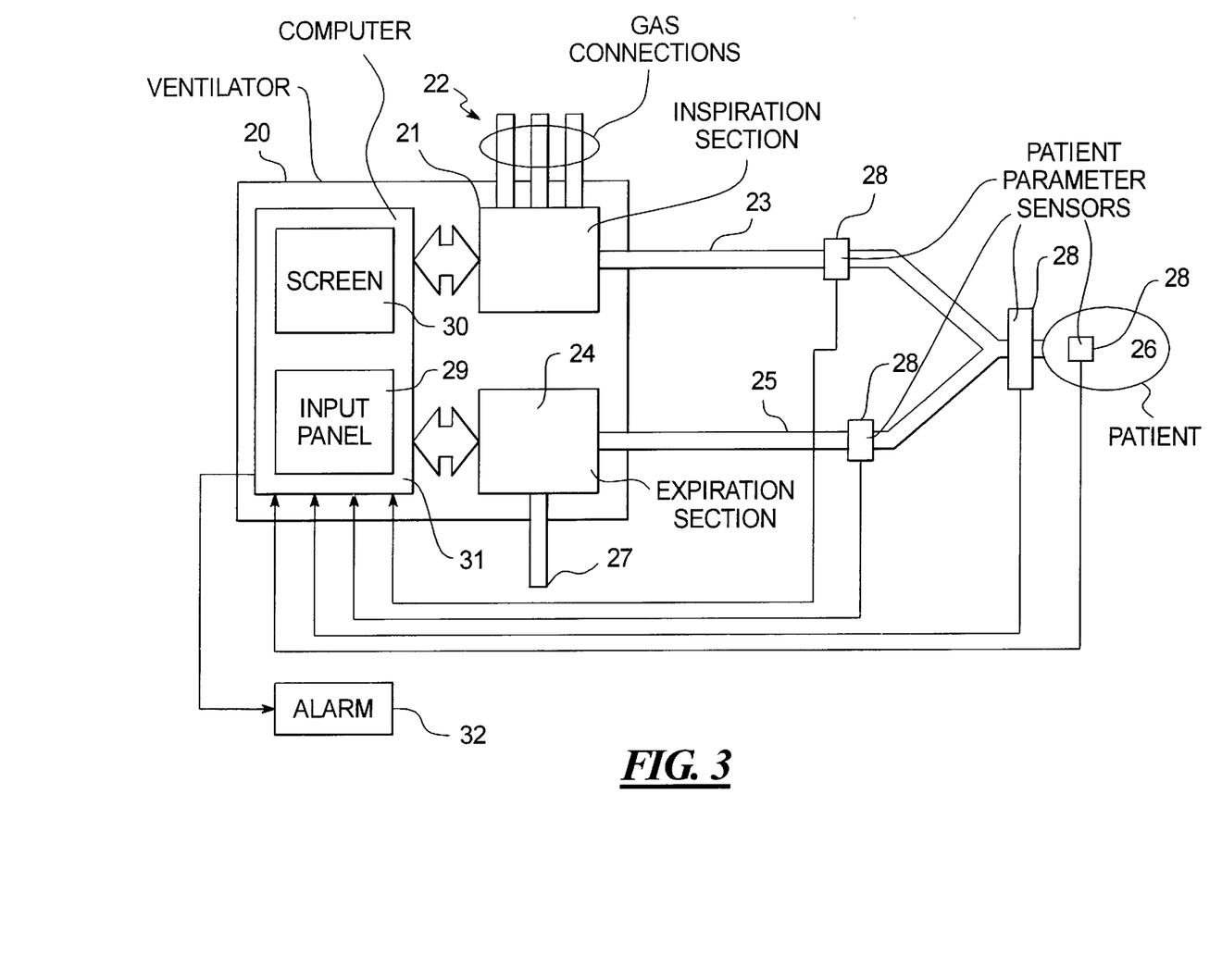
FIG. 3 is a schematic block diagram of a ventilator constructed and operating in accordance with the principles of the present invention.

Such a known system (with the exception of the operation of the computer, as described below) is shown in FIG. 3. A ventilator 20 has an inspiration section 21, supplied with breathing gas via gas connections 22, from which inspiratory gas is supplied via an inspiration line 23 to a patient 26. The ventilator 20 also has an expiration section 24 which receives expiratory gas from the patient 26 via an expiration line 25, and which has an evacuation conduit 27. Patient parameter sensors 28 supply information about the respiratory system of the patient 26 to a computer 31 in the ventilator 20, which makes use of this information in the manner described below. The computer has an input panel 29 and a display screen 30, which also are employed as described below. Under the circumstances also described below, the computer 31 supplies a signal to an alarm 32.

The mechanical properties of the respiratory system can be studied and defined as described above with known methods. In order to fulfil make possible a computer analysis of different modes of ventilation the mechanics during expiration must also be mathematically defined. This is done as described below.

The tracheal pressure has during mechanical ventilation of the sedated patient that has no own muscular activity two components, the elastic recoil pressure, Pel and the resistive pressure component, Pres:

$$Ptr = Pres + Pel \quad (3)$$

According to a preferred embodiment measurements are performed during insufflation of a modulated sinusoidal flow pattern. Utilising a known iterative technique the parameters of equation 1 and 2 are calculated. Thereby the elastic and resistive properties of the respiratory system under inspiration become known.

It is known from studies at health and in disease that the $P_{el}/V$ curve displays no significant hysteresis over ordinary or modestly increased tidal volumes. Accordingly, Eq. 1 can often be used to describe Pel as a function of volume both for inspirations and expirations.

Resistance differs often between inspiration and expiration. Expiratory resistance, R(e) can be determined according to the following:

For each sampling interval during one or more expirations R(e) is calculated first by calculation of Pres from Eq. 3, and then by dividing Pres by flow rate, F. F and Ptr are measured, while Pel is calculated from volume according to Eq. 1. The expiratory conductance G(e) is then calculated as 1/R(e). G(e) is approximately linearly correlated to volume:

$$G(e) = g0 + g1 * V \quad (4)$$

In order to avoid the influence by fast accelerations and decelerations at the flow transitions between inspiration and expiration the calculation of the coefficients g0 and g1 are based on a volume interval which does not include the start and end of the expiration that is studied.

In order to provide data for gas exchange the single breath test for $CO_2$ is analysed in a special format. The volume of $CO_2$, which is expired during the course of a breath, $Vt_{CO2}$ is calculated from the integral of the product between flow rate and $CO_2$ concentration. $Vt_{CO2}$ is related to expired volume, FIG. 1, panel 1. The upper part of the curve, indicated in heavy line, can with a high precision be described as a $2^{nd}$ degree equation:

$$Vt_{CO2} = a_{CO2} b_{CO2} \cdot Vt + c_{CO2} \cdot Vt^2 \quad (5)$$

Figure 1A:
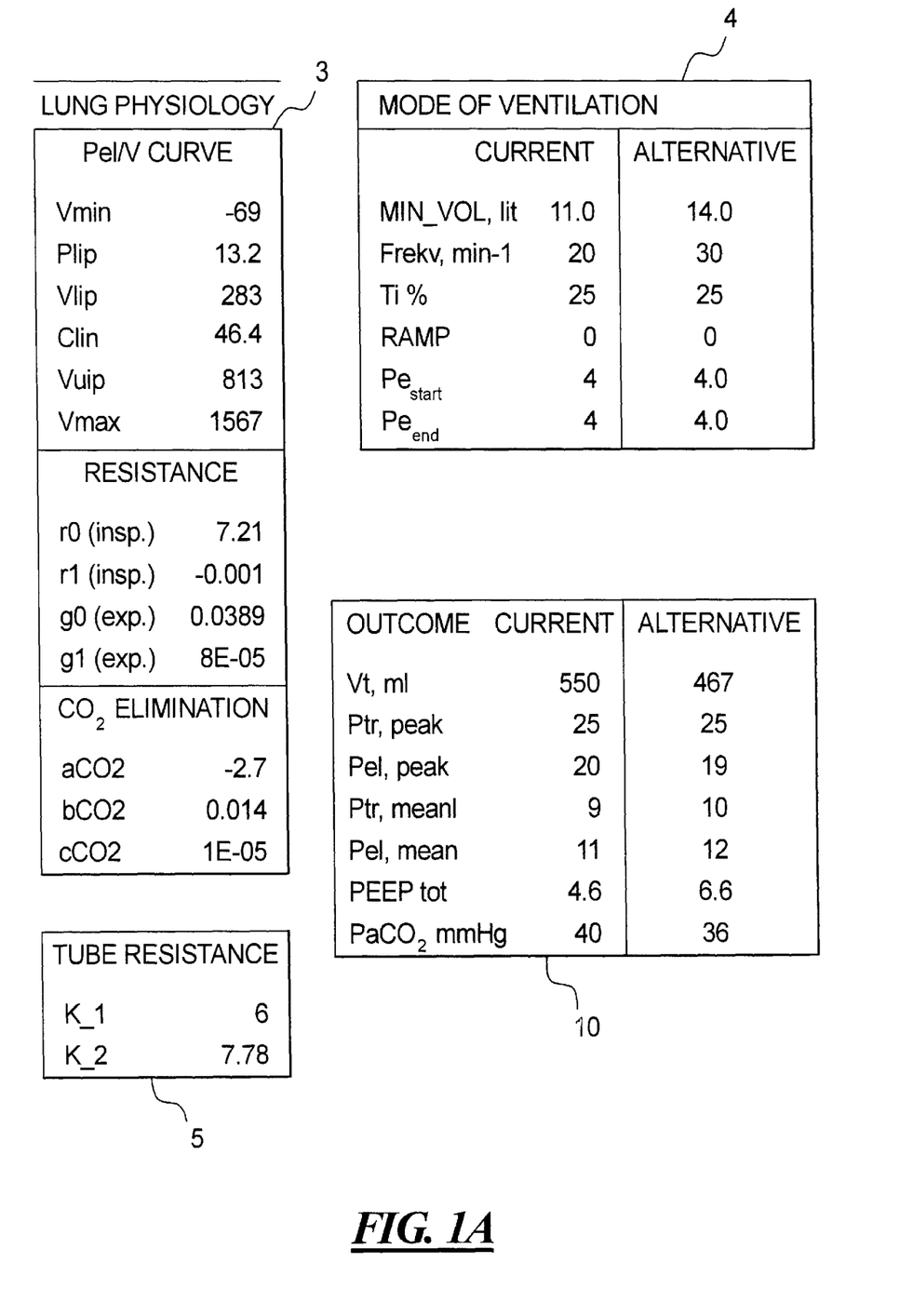
FIGS. 1A, 1B, 2A and 2B represent printouts of computer screens which arise during execution of the inventive method in an inventive apparatus.
Figure 2A:
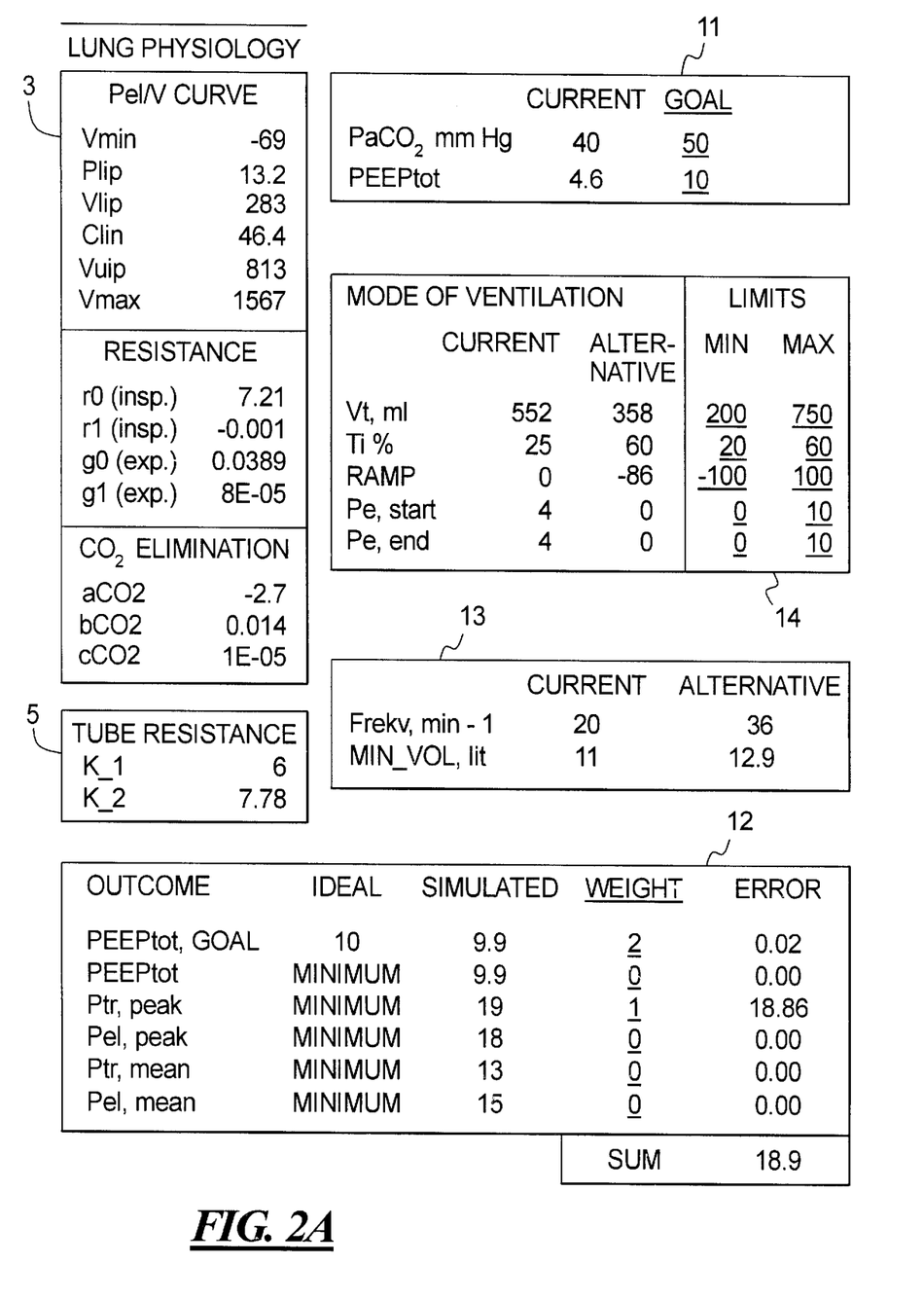

Equations 1–5 constitute the mathematical description of the respiratory physiology from which analyses and simulation of lung function is performed. The coefficients of the equations, presented in panel 3, FIGS. 1A and 2A, are automatically transferred from the Excel work sheet in which they are calculated to the work sheet in which further analysis is made.

The description of the physiological properties of the respiratory system can be expressed in equations which are alternatives to eq. 1–5. The mathematical description of respiratory mechanics and, according to a preferred embodiment also gas exchange, serve according to the invention as a basis for simulation of the course of physiological events that would follow a change in mode of ventilation. The description of the physiological properties of the respiratory system may be in the format of tables as well as equations. The methods employed for the description of the respiratory physiology may vary as long as they fulfil the demand the simulation process raises.

Simulations of mechanics and gas exchange, as they would appear after the establishment of an alternative mode of ventilation, can with the present system be performed from two different starting points.

Figure 1B:
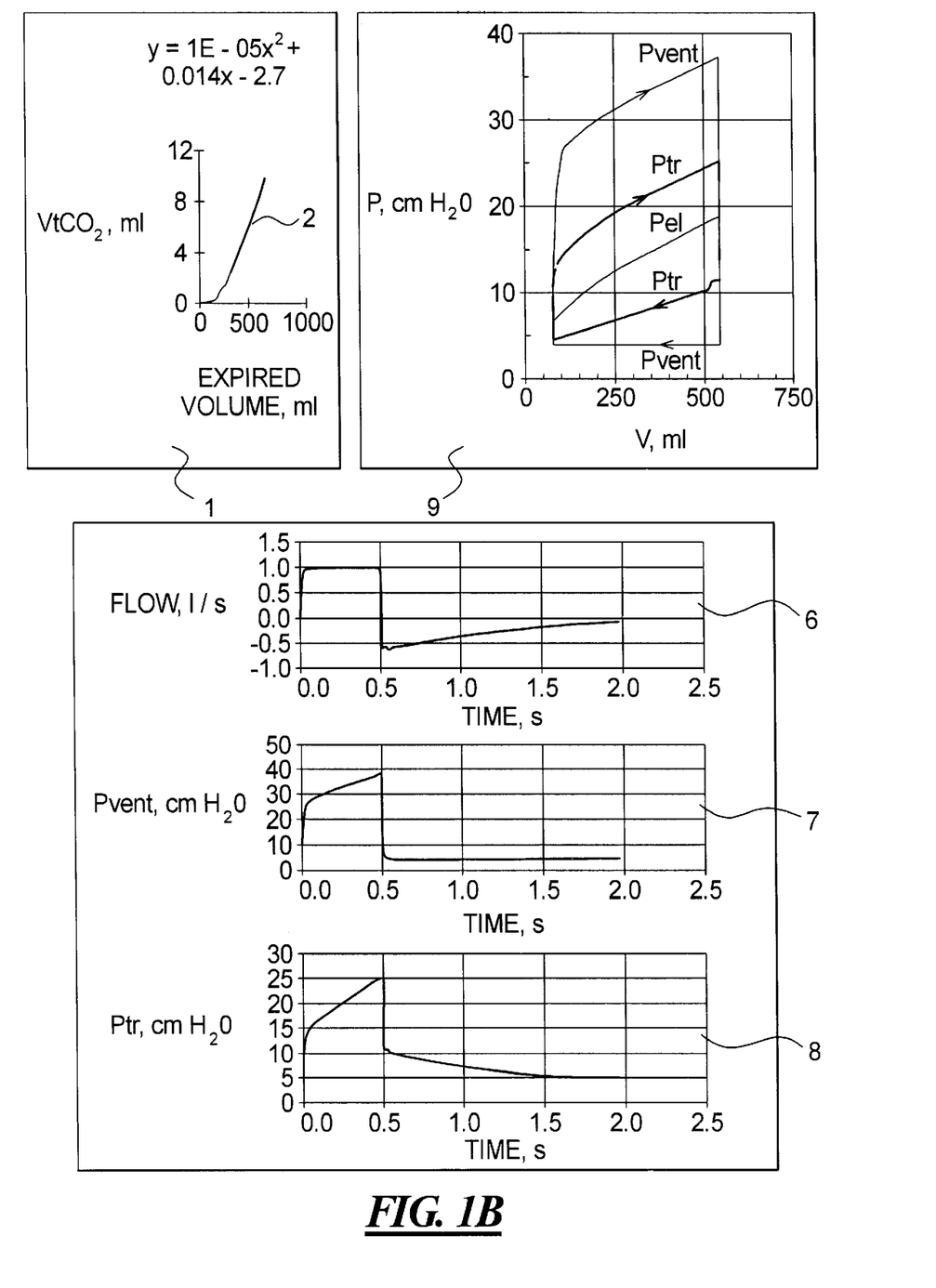

1. The operator defines an alternative mode of ventilation, which he wants to analyse with respect to mechanical consequences and gas exchange. The computer then performs the analysis and presents the results as shown in FIG. 1B. Then the operator considers if the analyzed mode of ventilation accords with the immediate therapeutic goal he has defined. The operator could also analyze further modes in order to find one that is deemed preferable with respect to the therapeutic goal.

2. The operator defines the therapeutic goal. The computer then performs an iterative search for a mode of ventilation, which leads as close as possible to the therapeutic goal. In this search limits of the parameters defining the mode of ventilation defined by the operator are respected.

Independent upon which starting points the invention is practised, the mathematical simulation of the events following a change of mode of ventilation follows the same principle. For each tested mode of ventilation six breaths are mathematically simulated in order to provide a steady state with respect to mechanical events, notably the volume and the pressure from which a breath starts. Simulation can be done for volume or pressure controlled ventilation. In this context volume controlled ventilation is further described.

The analysis starts from a mathematical description of the alternative mode of ventilation in terms of a number of parameters depicted in panel 3, FIG. 1A.

1. Minute volume, MIN_VOL.
2. Breathing frequency, Frekv. MIN_VOL and Frekv define together tidal volume, Vt: Vt=MIN_VOL/Frekv
3. Inspiratory time in % of the breathing cycle, Ti%.
4. Flow ramp during inspiration, RAMP. 0 implies a constant inspiratory flow rate. 100 implies that flow rate increases from zero to twice mean inspiratory flow. −100 implies that flow decreases from twice mean inspiratory flow to zero.
5. The pressure in the ventilator at start of expiration, $Pe_{start}$.
6. The pressure in the ventilator at end of expiration, $Pe_{end}$.

The simulation is performed by partitioning of each simulate breath into short time intervals. Most intervals are 1% of the breathing cycle. At the start of each phase of the breathing cycle the intervals are 1% of the breathing cycle in other to increase the precision of the simulation of transient events. During each interval, with the duration $\Delta t$, the process is simulated by a series of calculations, which are based upon the properties of the respiratory system and the function of the ventilator during the actual time interval or the immediately preceding interval. The resulting phase shift between different steps in the calculation, which may correspond to one time interval, does not lead to significant inconveniences as the intervals are short, in particular those around the transitions between inspirations and expirations.

For each time interval during the inspiration the flow rate from the ventilator, F, is first calculated from the frequency, Vt, Ti% and RAMP, as well as from the time of the interval in relation to the start of the inspiration. According to an alternative embodiment the flow pattern during inspiration is not simulated as a linear ramp but in accordance with an elective equation or a table. For example, the flow rate may initially during the inspiration increase linearly to reach an early maximum and then be given the form of an exponential decline. Independent upon which flow pattern is applied, F is corrected for the volume that does not leave the tubing in order to maintain the tracheal flow rate equal to Ftr in accordance to previously known principles. The volume, V, is during the complete simulation process by consecutively summing the product Ftr*$\Delta$t from the moment and from the volume of the lungs at the beginning of the measurement procedure of lung mechanics.

Then, Pel is calculated from V and the parameters defining the $P_{el}V$ curve according to Eq. 1. Pres(i) is calculated according to Eq. 2. Ptr is then calculated from Eq. 3. The pressure in the ventilator, Pvent, is calculated by adding to Ptr the pressure drop from the Y-piece to the trachea calculated by multiplication Ftr with the resistance of the tube at the actual value of Ftr. The resistance of the tube, Rtube, at a certain flow is calculated according to Rohrer's formula from the coefficients K_1 and K_2 shown in panel 5 in FIGS. 1A and 1B.

During simulated expirations and for each time interval the pressure controlled by the ventilator, Pe, is calculated. Pe is according to the preferred embodiment allowed to vary as a linear ramp from $Pe_{start}$ to $Pe_{end}$. Then, the expiratory flow is calculated as:

$$((Pel-Pe)/R(e)+Rtube).$$

Then, the volume is calculated as has been described for inspiration and also Pel according to Eq. 1. A new value for G(e) is calculated according to Eq. 4. G(e) is inverted to obtain R(e). For each time interval Rtube and Ptr are then calculated as has been described for the inspiratory phase.

After the simulation of one breath an additional number of breaths are simulated until the system comprising the ventilator and the respiratory system have come to a steady state with respect to pressure, flow and volume during succeeding breaths. The events during the last simulated breath constitute the result of the simulation. The result is presented in the format of curves over flow 6, of the pressure in the ventilator 7, and of Ptr 8, all plotted against time during the breath. Another presentation 9 shows Presp, Ptr and Pel plotted as a loop against volume changes during the breath. From the column Alternative in a panel 10 the following values constituting the outcome of the simulation are shown: Tidal volume Vt, peak and mean Ptr, peak and mean Pel and PEEPtot which is the pressure in the alveoli corresponding to Pel at the end of expiration. One may further read the value of $PaCO_2$, which is estimated to result at a steady state as described below.

A mode of ventilation that is considered to constitute an alternative to the one applied at the time t1 is below denoted alternative mode. Immediately after the institution of an alternative mode, at the time t2 $Vmin_{CO2}$ will change from the value $Vmin_{CO2}$(t1) to the value $Vmin_{CO2}$(t2). At a new steady state after 20 to 40 minutes, at the time t3 $PaCO_2$(t1) will have changed to $PaCO_2$(t3). The change of $PaCO_2$ within the period t1 to t3 is according to known principles indirectly proportional to the change of $Vmin_{CO2}$ from t1 to t2. The values of Vt at t1 and t2 are entered into equation 5. $VtCO_2$ can be calculated at these moments and then by multiplication with the frequency F at t1 and t2 also $Vmin_{CO2}$(t1) and $Vmin_{CO2}$(t2) are calculated. Then, $PaCO_2$(t3) is calculated:

$$PaCO_2(t3)=PaCO_2(t1)*Vmin_{CO2}(t1)/Vmin_{CO2}(t2) \quad (6)$$

If $PaCO_2$(t1) is unknown its value may be set to 1. Then, Eq. 6 will give $PaCO_2$(t3) in relationship to $PaCO_2$(t1).

The simulation of mechanics, and according to a preferred embodiment also of gas exchange, may according to the invention and according to the principle for calculation described above be performed from two perspectives. From one perspective the operator determines such alternative modes of ventilation that he intends to be-studied. The simulation by the computer is followed by the operator's judgement if the alternative mode of ventilation should be implemented or if further simulations should test other alternative modes.

The computer simulation according to the invention is performed with a program, which according to one embodiment is realised as a sheet for calculation of type Excel. A corresponding function may, however, be obtained with most programming languages.

FIG. 1 depicts the computer screen as it appears after a simulation. The content of the screen can easily be varied in order to be in harmony with the value an operator attributes to various partitions of the total information. According to the example of FIGS. 1A and 1B the operator has applied the perspective that he determines the mode of ventilation that he desires to analyse through simulation. He introduces values describing an alternative mode of ventilation in the column Alternative within the panel Mode of Ventilation 4, which mode he wants to analyse through simulation. Thereby he brings the program to analyse that mode. From FIGS. 1A and 1B it appears that the operator, as a comparison to the actual mode of ventilation, desired to analyse the outcome of a change of minute ventilation from 11 to 14 and a change of the frequency from 20 to 30. From the panel OUTCOME 10 he can among other observations note that the alternative mode is predicted to increase PEEPtot from 4.6 to 6.6 and to decrease $PaCO_2$ from 40 to 36. If the operator considers that this result corresponds to the therapeutic goals he intends to reach with an alternative mode of ventilation he may initiate such a mode. He might alternatively choose to enter further alternative in panel 4 and thereby simulate any number of alternative modes until he finds a mode, which with respect to expected result corresponds to his expectations.

Simulation of the events at pressure controlled ventilation is performed according to the same principles as at volume controlled ventilation. The difference is that for each time interval during inspiration the pressure generated by the ventilator, Presp, is first calculated from an equation describing how that pressure varies during inspiration. Presp minus Pel gives the pressure driving flow during the time interval. By dividing this pressure by the resistance in the tracheal tube and airways the inspiratory flow rate is obtained. The integral of the flow rate gives the volume change during the interval. From the volume Pel is then calculated according to eq. 1. Ptr is then calculated followed by calculation of a new value of Rtub. During expiration the simulation is performed as for volume controlled ventilation.

Going out from the second of above mentioned starting points simulation is performed within and iterative procedure serving to find that mode of ventilation, which as closely as possible corresponds to a predefined therapeutic goal. This goal may for a certain category of patients be defined by a programmed so called default. According to a preferred embodiment it is, however, the operator who defines the desired therapeutic GOAL. The GOAL may be of purely mechanical nature such as to achieve the lowest possible pressure in the patient's airways or alveoli. The GOAL may alternatively be a combination of results with respect to both mechanics and gas exchange. The importance of each component described by the GOAL may be weighted according to principles described below.

The lung is for gas exchange. Disregarding that an operator according to the preferred embodiment may choose and weigh different components comprising the GOAL, an embodiment based upon that the gas exchange should be assured to an extent defined by the operator is further described. From this prerequisite the simulation process seeks a mode in order to reach other components of the GOAL. In a patient ventilated by a ventilator the alveolar pressure at the end of expiration corresponds to Pel. This pressure is denoted total PEEP, PEEPtot. In order to maintain PLV PEEPtot should not fall below the pressure at which lung collapse occurs. Therefore a common component of the GOAL is to maintain a defined PEEPtot. Another component of the GOAL is that tracheal or alveolar peak pressure should be as low as possible in order to avoid barotrauma. A combination that maintains a defined PEEPtot and minimises peak pressure is important for PLV. In patients with severely compromised circulation it may, however, be important to decrease the mean tracheal or alveolar mean pressure. The preferred embodiment gives the operator a large degree of freedom to define the GOAL in terms of several components. Definition of the GOAL and the following simulation may follow the example illustrated in FIG. 2 showing a printout of the computer screen after a complete process of simulation.

The operator has defined the GOAL by filling in the column GOAL in panel 11 and by defining the weight of each partial goal in panel 12. Panel 11 shows that the operator according to the example desires to let $PaCO_2$ rise from 40 to 50 mm Hg. Furthermore, he wants that PEEPtot should increase from 4.6 to 10. Panel 12 shows that the operator attributed the partial goal to reach the desired PEEPtot a weight of 2 and to minimise peak tracheal pressure a weight of 1. Remaining pressures in panel 12 have been attributing the weight of zero. This implies that the values of these pressures do not influence the process of simulation. The significance of the concept weight is further explained below.

When the operator according to the preferred embodiment has noted that a partial goal is to achieve a certain $PaCO_2$ the degrees of freedom of the iterative process is limited to such alternative which satisfies the condition that the given $PaCO_2$ is achieved. The program attributes accordingly the given value $PaCO_2$ a weight that in principle is infinite. This effect is achieved in the following way.

The value of $PaCO_2$, defined as goal by the operator corresponds to $PaCO_2(t3)$ in equation 6. In the same equation $PaCO_2(t1)$ and $Vmin_{CO2}(t1)$ correspond to actual known values. $Vmin_{CO2}(t2)$ is the only unknown entity in the equation and may accordingly be calculated. In the iterative process alternative values of Vt are tested in the search for an alternative mode of ventilation. The examination of a certain value of Vt starts with a calculation of $VtCO_2$ at the moment (t2) according to equation 5. The Frequency is calculated as the quotient $Vminc_{CO2}(t2)/Vt_{CO2}(t2)$. The minute ventilation is then calculated as Vt*Frequency. In the described manner the given value of $PaCO_2$ is at a tested value of Vt coupled to given values of Frequency and minute ventilation. This implies that only such combinations of Vt, Frequency and minute ventilation, which satisfies the demand that $PaCO_2$, after initiation of an alternative mode and the establishment of a steady state, will reach the value $PaCO_{2,GOAL}$. The values of Frequency and minute ventilation, which are calculated from the target $PaCO_2$ and the value of Vt found by simulation, are presented in panel 13.

The analytical method used for calculation of Frequency and minute volume from an alternative value of Vt implies that the number of parameters describing the mode of ventilation analysed in the iterative process is reduced by one. This gives advantages in the form of less time consumption and improved security with respect to convergence of the iterative procedure toward a solution satisfying the goal determined by the operator. Similar results may in principle be achieved according to other embodiments allowing the iterative process to vary independently two of the factors Vt, Frequency and minute ventilation. Convergence of the iterative process toward a goal implying that a certain $PaCO_2$ should be reached may be achieved by entering $PaCO_2$ among other partial goals in panel 12 and by attributing this partial goal a high weight.

Apart from defining the goal as described the operator may enter the parameters describing the mode of ventilation, which are allowed to be changed. There are furthermore reasons for limitation of the change of the parameters. One reason is that the validity of description of the function of the respiratory system according to panel 3 is greater within a limited range of modes of ventilation than within a larger range. Another reason may be that the ventilator used may have technical limitation with respect to variability of the mode of ventilation. A third reason may be that tradition and experience are restricted to a limited range of mode of ventilation. For example, a negative experience from a particular category of patients may merit limitation of the allowed mode of ventilation by entering limits for changes of each parameter describing the mode of ventilation. It should also be mentioned that a limitation of allowed changes of the parameters is further merited by the existence of so called "local minima of the error signal". Such minima are particularly present at extreme combinations of the parameters which are allowed to vary. Risks associated with convergence of the numerical process toward a non-relevant minimum may be practically eliminated by limiting the range of allowed variation of the parameters describing the mode of ventilation.

Figure 2B:
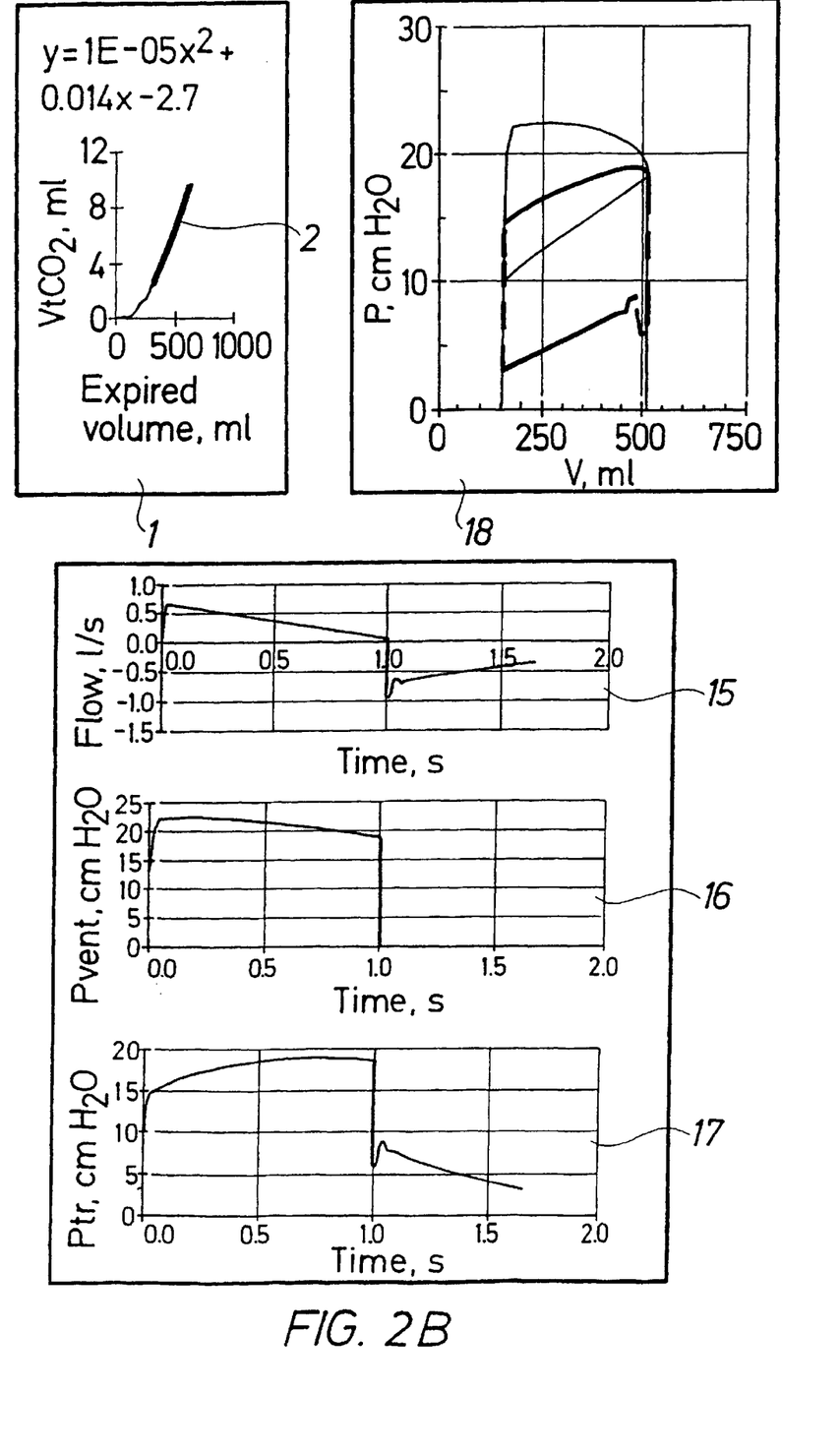

According to the embodiment depicted in FIGS. 2A and 2B, parameters describing the mode of ventilation are described in panel 14 together with the limits within which the parameters are allowed to vary. The operator may change these limits presented as their default values. Accordingly, he needs only to enter aberrations from the default values.

The system based upon default may according to the invention be used to facilitate for the operator to use the system, by calling for menus specific for particular groups of patients and situations to be presented on the computer screen. One may for example call upon a menu intended for ARDS patients. In this menu a partial goal might be a value of PEEPtot calculated from the coefficients in panel 3 describing the Pel/V curve of the patient. This goal may be attributed a high weight. One may follow a tradition aiming at limitation of peak Ptr, $Ptr_{peak}$. Starting from a menu of this character, which is intended for ARDS patients, the operator only needs to determine if $PaCO_2$ should be maintained at the current value or if it should be changed. Accordingly, by calling upon a menu for ARDS patients, which is defined in the treatment protocol of the establishment, it is possible even for a modestly experienced operator to make use of the system.

If the patient suffers from severe obstructive lung disease the goal may be to reduce $PaCO_2$ while, on the same time one seeks a setting, which gives the lowest possible pressure in the alveoli at the end of expiration, i.e. PEEPtot. In that particular situation a menu may be called upon in which by default values such goals are predefined and weighted.

In a preferred embodiment of the invention default values for different groups of patients are combined with freedom for the trained operator to modify default values in accordance with his experience and knowledge.

When the operator has defined the GOAL and the limits for alternative modes of ventilation he starts the iterative estimation of such a mode that in an optimal way leads towards the GOAL. Within the iterative process such a combination of parameters describing the mode of ventilation, which leads to a minimum of a parameter denoted ERROR, is sought. ERROR is calculated from deviations of those partial goals, which the operator has defined or accepted as default. The outcome is read from the last breath of the simulation. ERROR is the sum comprising components from each partial goal.

For a partial goal, which reflects that a certain value of a parameter describing the outcome should be reached, a primary error is calculated as the deviation between the defined partial goal in panel 12, which is denoted Ideal, and the value of the parameter, which represents the outcome of the simulation, denoted Simulated in panel 12. This primary error is attributed a positive sign either by taking the absolute value of the error or by raising the error to the second power. According to a preferred embodiment, in a situation in which PEEPtot should attain a certain value the error of PEEPtot is calculated by raising the deviation to the second power before the resulting error is multiplied by the factor WEIGHT. Thereby one achieves that small deviations contribute little to ERROR while large deviations contribute much. This is advantageous within the iterative process as this process more efficiently converges towards an optimal solution. When the operator wants that the target PEEPtot should be accomplished with a high precision he attributes the partial goal PEEPtot a relatively high weight according to the example in panel 12, FIG. 2A.

In order to achieve that a partial goal in panel 12, which reflects that a parameter describing the outcome should be brought to a minimum, the primary error is calculated as the deviation between the defined partial goal and the simulated value of the parameter. Thereafter, this primary error is multiplied by the weight the operator has attributed the error. The contribution by each partial error to the total error is presented in the column ERROR in panel 12. This is also the case with respect to their sum, which as described is denoted ERROR.

As is shown by the embodiment illustrated in FIG. 2A panel 12, the partial goal with respect to PEEPtot may be to maintain a certain target value or to minimise the value. Other values for which minimal values may be sought are peak and mean values of Ptr and Pel. The operator may as shown be free to choose a combination of parameters, which together define the GOAL. He does so by attributing the error for different parameters a weight greater than zero. In order to make different errors equally important and to make them independent upon which denomination they are expressed in, it is according to the invention possible to normalise the primary error for each parameter in such a way that they in a typical situation will contribute to the error to the same extent if the operator has attributed them the same weight.

When, as described, the operator has defined the partial therapeutic goals as well as the limits for alternative modes of ventilation he starts an iterative simulation process. In a numerical process the computer seeks the mode of ventilation, which leads to the lowest value of ERROR. Several methods for iterative estimation of parameters are known and commonly used. According to experience, the iterative estimation of parameters describing the mode of ventilation, which minimises ERROR, is in the preferred embodiment based upon a principle commonly denoted Newton's. The principle is applied by successive approximations based upon linear tangents in the multidimensional sphere of data. Computer tools for such estimations are available in several commercially available programs. In a preferred embodiment the tool Solver (EXCEL 5.0 Microsoft) was used.

The results of the simulation are presented for the operator both in terms of parameters describing the mode of ventilation, which according to the simulation leads as closely as possible to the by the operator defined GOAL. These parameters are shown in FIG. 2A, panel 14, column Alternative. According to the preferred embodiment also the predicted course of a breath is displayed in diagrams over time showing flow rate 15, Pvent 16 and Ptr 17. Furthermore, a diagram 18 is shown, depicting the pressure in the ventilator, Ptr and Pel presented as loops against the volume V during the breath. The operator analyses the outcome of the simulation and considers if the outcome with respect to security and the medical reasons is such that a change of mode of ventilation in accordance with the simulation can be expected to lead to the defined therapeutic goals. The operator further judges if this mode of ventilation can be expected to benefit the patient from a comprehensive perspective. If that is the case he may initiate a change of the mode of ventilation in accordance with the simulation. If he finds that further alternative need to be explored he may after modification of the GOAL of the limits for parameters describing the mode of ventilation repeat the simulation and on the basis of the new simulation again consider if an alternative mode of ventilation can be expected to benefit the patient. The operator may also manually modify the parameters describing the mode of ventilation according to the simulation. Such modification is automatically followed by a new simulation and presentation of the outcome of such a modified mode of ventilation. The operator may again judge if the latter outcome can be used as a basis for an alternative mode of ventilation. If so, he may initiate that mode.

At pressure controlled ventilation Vt is a result of the course of Presp during the breathing cycle. Accordingly, Vt is unknown at the start of a simulation process. At simulation of pressure controlled ventilation with the goal to maintain a certain value of $PaCO_2$, this cannot be reached by limiting the iterative process to such modes of ventilation, which leads to the desired value of $PaCO_2$. In this situation $PaCO_2$ is dealt with according to principals corresponding to those above described for PEEPtot according to the preferred embodiment. This implies that the difference between desired value for $PaCO_2$ and the value obtained through simulation is raised to the $2^{nd}$ power and is attributed a relatively high weight. Thereby, to a corresponding degree, all deviations will give an important positive contribution to ERROR.

According to a preferred embodiment the computer, which is used for studies of the respiratory system physiology, is also used for the simulation of alternative modes of ventilation. The system used for such purposes has been described in the aforementioned thesis and article. An advantage of this embodiment is that it takes no system for transfer of data describing the physiology of the respiratory system from a measurement system to the computer used for simulations. Other advantages may, however, be reached through alternative embodiments. The simulation may be independent upon the measurement system, which another apparatus and at another place. After transmission of data describing the situation of the patient and his physiology experts in respiratory care may perform simulation and on the basis of these contribute to improved respiratory care without being present at bedside.

The characterisation of the mechanics of the respiratory system as described above may cover a volume and elastic pressure range far above and below the volume range of the current tidal volume. As an alternative mode of ventilation may reach into these zones this may be an advantage, as the physiology over the alternative volume range is then known. However, in some conditions like ARDS, the physiology may immediately change from that prevailing during normal tidal volume when a wider range of volume is studied. The elastic pressure volume curve will change as a result of a reduction of lung volume at which airway closure and alveolar collapse occurs. Under such conditions, the $P_{el}V$ curve studied with a starting point at low lung volumes will not be valid during tidal ventilation at higher lung volumes. An alternative embodiment of the invention has been developed in order to avoid these problems. In this alternative embodiment the physiology of the respiratory system is studied during ventilation with volumes which do not cover such a volume range that the physiology is significantly changed by the measurement procedure. Preferably, in the alternative embodiment respiratory physiology is studied just within the current tidal volume range. In the alternative embodiment flow rate, airway pressure and carbon dioxide the computer records signals for a certain number of consecutive breaths. For at least one breath the pressure following a postexpiratory pause and a postinspiratory pause is recorded. The analysis of the sequence of breaths, most of which may be ordinary breaths, starts with a computer identification of the pauses mentioned and reading of the postinspiratory pressure, denoted plateau pressure, Pplat, and the postexpiratory alveolar pressure denoted PEEPtot. The elastic pressure volume curve is considered to be linear within the limited volume range corresponding to the tidal volume. This is known to be a reasonable approximation. The course of the tracheal pressure during the breaths is calculated as described above. The conductance of the respiratory system, G, is for each moment calculated as:

$$G = \text{Flow}/(Ptr - Pel) \tag{7}$$

Conductance and its variation with lung volume during inspiration and during expiration are calculated as separate linear equations. The perturbed data at transitions between inspiration and expiration are not included in this calculation. The exchange of $CO_2$ is analysed as described above. The data describing the physiology of the ordinary breath are transferred to the simulation program. An advantage of a more simple mathematical description of the physiology of the respiratory system is that the simulation process may be simplified. The use of continuous and often linear equations makes simulations possible with analytic rather than by numerical techniques. When numerical techniques nevertheless are employed the iterative simulations more easily converges toward, a true minimum. An other advantage of the alternative embodiment is that the measurement procedure is not associated with any significant deviations from the current breathing pattern. This eliminates potential hazards associated with particularly low and high airway pressures. The measurement procedure can be repeated at frequent intervals and be completely automated. The validity of data is increased with respect to the current volume and pressure range. However, extrapolation outside this range is associated by potential errors. Accordingly, the initiation of modes of ventilation, which are very different from the current mode based upon simulations, may lead to unpredictable results. Repeated measurements and simulation procedures as further described below may, however, compensate for this potential drawback.

The simulation program of the alternative embodiment based upon tidal volume analysis follows the principles described above. However, after execution of the simulation according to either of the two starting points, the initiation of an alternative mode of ventilation may if so decided by the operator be realized in a stepwise manner. The operator may enter the number of steps and the time interval between the steps by which the alternative mode should be realised. Then, the computer suggests a new mode of ventilation by interpolation in between the parameters describing the current ventilator setting and the alternative obtained through simulation. In a preferred embodiment each step is preceded by a new study of the respiratory physiology and a repeated simulation procedure.

The operator may initiate and define a process through which the alternative mode is introduced stepwise in a manual, or alternatively in fully or partially automated procedure. A typical setting would be that the initial measurement and simulation procedure is followed by a change in mode of ventilation such that for each parameter describing the mode the gap between current setting and the setting suggested from simulations is reduced by for example 25 or 50%. After an interval defined by the operator the measurement and simulation procedure is repeated. Thereby a successive approach toward a mode of ventilation that in an optimal way leads to the goal defined by the operator is achieved. The computer is equipped with means for controlling the function of the ventilator as is previously described in the aforementioned article and thesis. By emitting signals to the ventilator the computer can override the settings on the front panel of the ventilator. These means makes it possible to let the computer effectuate changes of mode of ventilation within wide technical limits. However, as described above the operator defines the limits within which he allows changes of parameters describing the mode of ventilation. The procedure may according to the operator's decision be automated with or without operator surveillance.

Although modifications and changes may be suggested by those skilled in the art, it is the intention of the inventor to embody within the patent warranted hereon all changes and modifications as reasonably and properly come within the scope of his contribution to the art.

Figure 4:
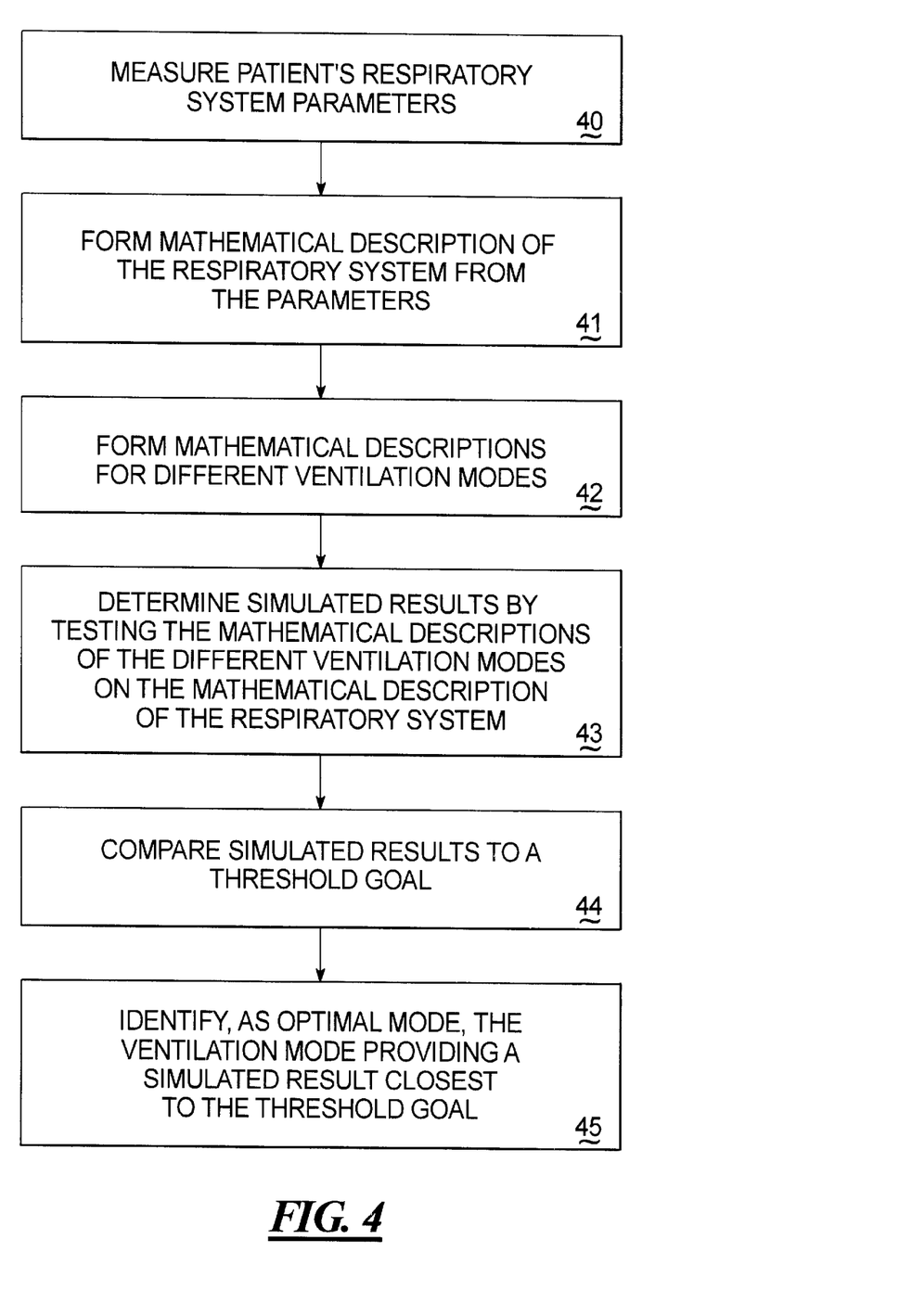
FIG. 4 is a flowchart illustrating the basic steps of the inventive method.
Figure 5:
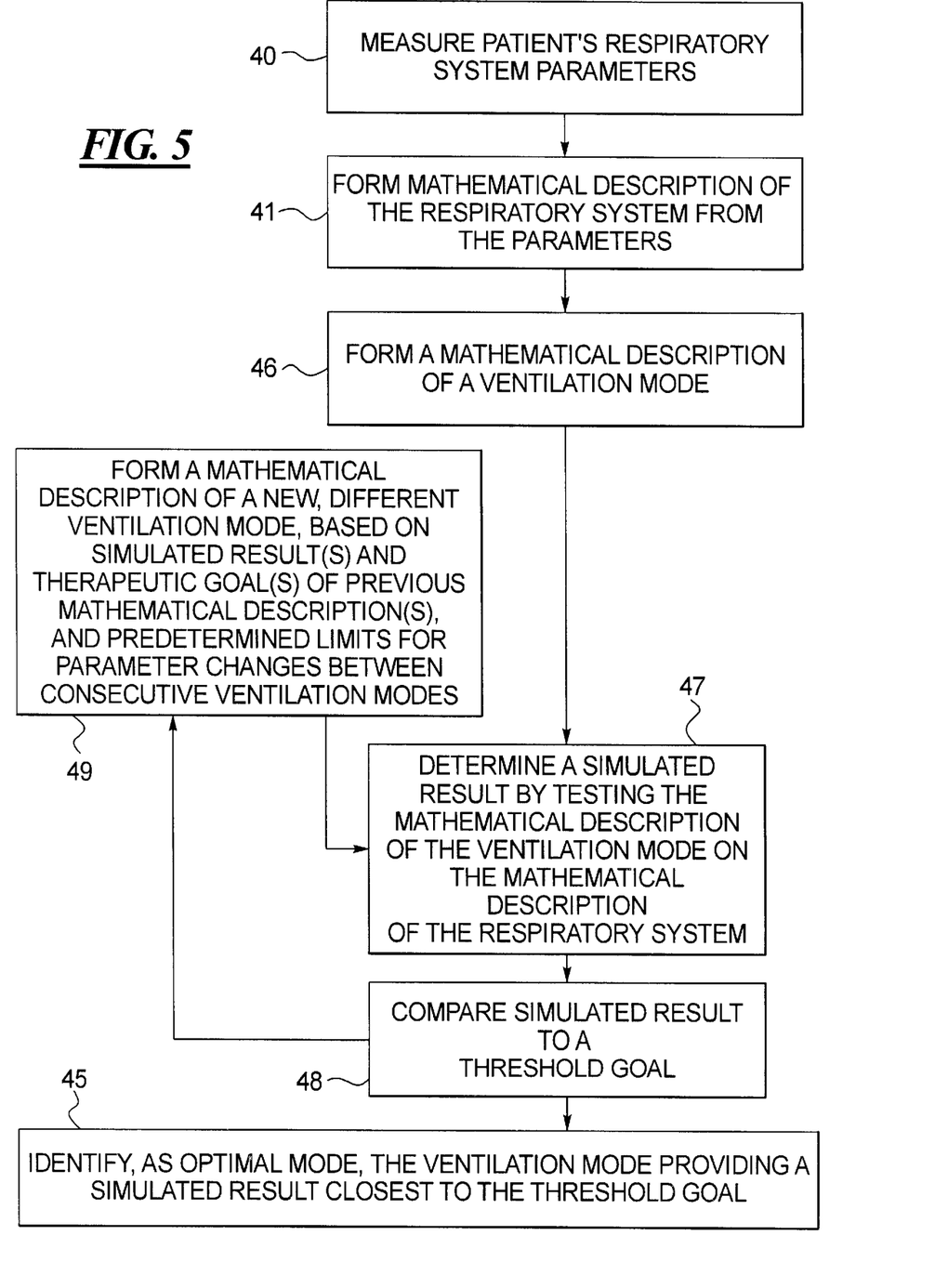
FIG. 5 is a flowchart illustrating the basic steps of an alternative version of the inventive method.

The above-described inventive method is summarized in the flowcharts shown in FIGS. 4 and 5.

In FIG. 4, in a first step 40, the patient's respiratory system parameters are measured, and in step 41 a mathematical description of the respiratory system is formed from these parameters. In step 42 mathematical descriptions for different ventilation modes are formed. In step 43, simulated results are determined simultaneously (i.e. in parallel) by testing the mathematical descriptions of the different ventilation modes on the mathematical description of the respiratory system. In step 44 the simulated results are compared to a threshold goal, and in step 45 a ventilation mode is identified, as the optimal mode, which provides a simulated result closest to the threshold goal.

In the version of the inventive method shown in FIG. 5, steps 40 and 41 are the same as in FIG. 4. In the version illustrated in FIG. 5, in step 46 a mathematical description of a ventilation mode is formed. In step 47 a simulate result is determined by testing the mathematical description of the ventilation mode, formed in step 46, on the mathematical description of the respiratory system, and this simulated result is compared to a threshold goal in step 48. In step 49 a mathematical description of a new, different ventilation mode is then formed, based on the simulated result (or results) and therapeutic goal (or goals) of one or more previous mathematical descriptions, and predetermined limits for parameter changes between consecutive ventilation modes. Steps 47, 48 and 49 are then looped-through for as many new, different ventilation modes as desired. A number of simulated results are thereby obtained, and then step 45 is executed to identify the optimal mode, in the same manner as in FIG. 4.

I claim:

1. A method of searching for an optima mode of ventilation from a plurality of modes of ventilation in a ventilator, comprising the steps of:

measuring parameters related to properties of a respiratory system of a patient;

forming a mathematical description of the respiratory system based on the measured parameters;

forming mathematic descriptions for different modes of ventilation, testing the mathematical descriptions for different modes of ventilation on the mathematical description of the respiratory system for determining simulated results, comparing the simulated results with a therapeutic goal to be achieved, and identifying the mode of ventilation providing a simulated result which comes closest to the therapeutic goal as the optimal mode.

2. A method according to claim 1, comprising determining the simulated result for a selected number of different modes of ventilation and selecting an optimal mode of ventilation among the selected number of different modes of ventilation.

3. A method according to claim 2, comprising basing the mathematical description of the respiratory system on measured parameters relating to elastic and resistive properties of the respiratory system.

4. A method according to claim 2, comprising basing the mathematical description of the respiratory system on measured parameters relating to gas exchange of the respiratory system.

5. A method according to claim 1, comprising basing the mathematical description of a respiratory system on measured parameters relating to elastic and resistive properties of the respiratory system.

6. A method according to claim 1, comprising basing the mathematical description of a respiratory system on measured parameters relating to gas exchange of the respiratory system.

7. A searching an optimal mode of ventilation from a plurality of modes of ventilation in a ventilator, comprising the steps of:

measuring parameters related to properties of a respiratory system of a patient, forming a mathematical description of the respiratory system based on the measured parameters;

forming a mathematical description of a mode of ventilation, testing the mathematical description for the mode of ventilation on the mathematical description of the respiratory system for determining a simulated result, comparing the simulated result with a therapeutic goal to be achieved, performing an iterative analysis by forming a new mathematical description of a new mode of ventilation, different from said mode of ventilation, by testing the new, different mode of ventilation on the mathematical description of the respiratory system for determining a new simulated result of the new different mode of ventilation and comparing the new simulated result with the therapeutic goal, whereby each new mathematical description for each new, different mode of ventilation is based on the therapeutic goal, the comparison between the simulated result and therapeutic goal of previously applied mathematical descriptions and predetermined limits for a change in parameters between two consecutive new, different modes of ventilation, and identifying the mode of ventilation providing a simulated result which comes closest to the therapeutic goal as the optimal mode.

8. An apparatus for searching for an optimal mode of ventilation for a patient, comprising a ventilator for providing treatment according to a current mode of ventilation to a patient, sensors for measuring parameters related to properties of a respiratory system of the patient and a computer, the computer being programmed to form a mathematical description of the respiratory system of the patient based on parameters related to the properties of the respiratory system measured by the sensors, to form a mathematical description of an alternative mode of ventilation and to test the mathematical description of the alternative mode of ventilation on the mathematical description of the respiratory system to determine a simulated result, and to receive information defining a therapeutic goal to be achieved, to determine the simulated result of a plurality of alternative modes of ventilation and to identify an alternative mode of ventilation providing a result which comes closest to the therapeutic goal as the optimal mode of ventilation.

9. An apparatus according to claim 8, comprising a panel operatively connected to the computer for entering the therapeutic goal and/or alternative modes of operation.

10. An apparatus according to claim 6, comprising a screen for displaying at least one of the therapeutic goal and the optimal mode of ventilation.

11. An apparatus according to claim 6, the computer is programmed to command the ventilator to alter the current mode of ventilation to the selected optimal mode of ventilation in one or several steps.

12. An apparatus according to claim 9, wherein the computer is programmed to determine a physiological result of the optimal mode of ventilation on the respiray system based on parameters measured by the sensor.

13. An apparatus according to claim 10, the computer is programmed to compare the physiological result with at least one of the therapeutic goal and the simulated result of the optimal mode of ventilation and if the physiological result deviates from at least one the herapeutic goal and the simulated result of the optimal mode of ventilation by a predetermined magnitude, to generate an alarm.

* * * * *